United States Patent [19]

Sasaki et al.

[11] Patent Number: 4,554,111
[45] Date of Patent: Nov. 19, 1985

[54] α-HYDROXYETHYLPHOSPHINATES, AND THEIR PRODUCTION AND USE

[75] Inventors: Mitsuru Sasaki, Osaka; Yukio Ishiguri, Hyogo, both of Japan

[73] Assignee: Sumitomo Chemical Company, Limited, Osaka, Japan

[21] Appl. No.: 642,771

[22] Filed: Aug. 21, 1984

Related U.S. Application Data

[62] Division of Ser. No. 487,670, Apr. 22, 1983.

[30] Foreign Application Priority Data

Apr. 26, 1982 [JP] Japan ............................... 57-71072
Jun. 8, 1982 [JP] Japan ............................... 57-98982
Dec. 1, 1982 [JP] Japan ............................... 57-211815

[51] Int. Cl.$^4$ ............................................. C07F 9/48
[52] U.S. Cl. ............................................. 260/502.4 R
[58] Field of Search ................................ 260/502.4 R

[56] References Cited

FOREIGN PATENT DOCUMENTS 0113190 7/1984 European Pat. Off. ...... 260/502.4 R

OTHER PUBLICATIONS

Kosolapoff, "Organophosphorus Compounds", 1950, pp. 129–132, 146, 147 and 154–157.
Von Wazer, "Phosphorus and Its Compounds", vol. 1, Chemistry, 1958, pp. 348–352.

Primary Examiner—J. E. Evans
Attorney, Agent, or Firm—Birch, Stewart, Kolasch & Birch

[57] ABSTRACT

A compound of the formula:

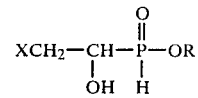

wherein X is a hydrogen atom, a chlorine atom or a bromine atom and R is an alkyl group, a lower haloalkyl group, a lower cycloalkyl group, a lower alkoxy(lower)alkyl group, a lower alkylthio(lower)alkyl group, a phenoxy(lower)alkyl group, a phenylthio(lower)alkyl group, a phenyl(lower)alkoxy(lower)alkyl group, a phenyl(lower)alkylthio(lower)alkyl group, a lower cycloalkyl(lower)alkyl group, a lower alkyl(lower)cycloalkyl group, a halo(lower)cycloalkyl group, a lower alkylthio(lower)cycloalkyl group, a lower alkoxy(lower)cycloalkyl group, a lower cycloalkyl(lower)cycloalkyl group, a lower alkoxy(lower)alkoxy(lower)alkyl group, a phenyl(lower)alkyl group, a halophenyl(lower)alkyl group, a lower alkylphenyl(lower)alkyl group, a lower alkoxyphenyl(lower)alkyl group, a phenoxyphenyl(lower)alkyl group, a phenylphenyl(lower)alkyl group, a dihalophenyl(lower)alkyl group, a di(lower)alkylphenyl(lower)alkyl group, a di(lower)alkoxyphenyl(lower)alkyl group, a tri(lower)alkoxyphenyl(lower)alkyl group, a naphthyl(lower)alkyl group or an anthracenyl(lower)alkyl group, which is useful as a fungicide.

1 Claim, No Drawings

α-HYDROXYETHYLPHOSPHINATES, AND THEIR PRODUCTION AND USE

This application is a divisional of copending application Ser. No. 487,670, filed on Apr. 22, 1983.

The present invention relates to α-hydroxyethylphosphinates, and their production and use.

The said α-hydroxyethylphosphinates are representable by the formula:

$$XCH_2-\underset{\underset{OH}{|}}{CH}-\underset{\underset{H}{|}}{\overset{\overset{O}{\|}}{P}}-OR \qquad (I)$$

wherein X is a hydrogen atom, a chlorine atom or a bromine atom and R is an alkyl group, a lower haloalkyl group, a lower cycloalkyl group, a lower alkoxy(lower)alkyl group, a lower alkylthio(lower)alkyl group, a phenoxy(lower)alkyl group, a phenylthio(lower)alkyl group, a phenyl(lower)alkoxy(lower)alkyl group, a phenyl(lower)alkylthio(lower)alkyl group, a lower cycloalkyl(lower)alkyl group, a lower alkyl(lower)cycloalkyl group, a halo(lower)cycloalkyl group, a lower alkylthio(lower)cycloalkyl group, a lower alkoxy(lower)cycloalkyl group, a lower cycloalkyl(lower)cycloalkyl group, a lower alkoxy(lower)alkoxy(lower)alkyl group, a phenyl(lower)alkyl group, a halophenyl(lower)alkyl group, a lower alkylphenyl(lower)alkyl group, a lower alkoxyphenyl(lower)alkyl group, a phenoxyphenyl(lower)alkyl group, a phenylphenyl(lower)alkyl group, a dihalophenyl(lower)alkyl group, a di(lower)alkylphenyl(lower)alkyl group, a di(lower)alkoxyphenyl(lower)alkyl group, a tri(lower)alkoxyphenyl(lower)alkyl group, a naphthyl(lower)alkyl group or an anthracenyl(lower)alkyl group.

In the above significances, the number of carbon atoms in the alkyl group is not more than 13. The term "lower" is generally intended to have not more than 8 carbon atoms, and the term "halo" is intended to mean chlorine, bromine, fluorine and iodine, inclusively. Preferred examples of R include $C_1$–$C_{10}$ alkyl, $C_2$–$C_3$ haloalkyl, $C_5$–$C_6$ cycloalkyl, $C_1$–$C_3$ alkoxyethyl, $C_1$–$C_2$ alkylthioethyl, phenoxyethyl, phenylthioethyl, phenylmethoxyethyl, phenylmethylthioethyl, $C_3$–$C_6$ cycloalkylmethyl, methylcyclohexyl, chlorocyclohexyl, methylthiocyclohexyl, methoxycyclohexyl, cyclohexylcyclohexyl, methoxyethoxyethyl, benzyl, halobenzyl, $C_1$–$C_4$ alkylbenzyl, $C_1$–$C_4$ alkoxybenzyl, phenoxybenzyl, phenylbenzyl, dichlorobenzyl, dimethylbenzyl, dimethoxybenzyl, trimethoxybenzyl, phenyl($C_2$–$C_3$)alkyl, chlorophenethyl, methoxyphenethyl, methylphenethyl, naphthyl($C_1$–$C_2$)alkyl and anthracenylmethyl.

Various fungicides having only a preventive effect have been used for control of plant diseases such as late blight and downy mildew which are caused by infection of Phycomycetes. However, their practical use was limited, since a sufficient controlling effect was hardly produced after the invasion of pathogenic fungi into plant bodies.

It has now been found that the α-hydroxyethylphosphinates (I) show not only a preventive effect but also a curative effect against plant diseases such as late blight and downy mildew caused by infection of Phycomycetes. Thus, they are useful as fungicides.

Examples of phytopathogenic fungi belonging to Phycomycetes, against which the α-hydroxyethylphosphinates (I) can exert their fungicidal activity, are as follows: *Peronospora brassicae* on vegetables and radish, *Peronospora spinaciae* on spinach, *Peronospora tabacina* on tobacco, *Pseudoperonospora cubensis* on cucumber, *Plasmopara viticola* on grape, *Plasmopara nivea* on Umbelliferae plants, *Phytophthora cactorum* on apple, strawberry and carrot, *Phytophthora capsici* on tomato and cucumber, *Phytophthora cinnamomi* on pineapple, *Phytophthora infestans* on potato, tomato and eggplant, *Phytophthora nicotianae* var. *nicotianae* on tobacco, kidney bean and onion, *Pythium aphanidermatum* on cucumber, Pythium sp. on spinach, Pythium sp. on wheat, *Pythium debaryanum* on tobacco, Pythium rot (i.e. *P. aphanidermatum, P. debaryanum, P. irregulare, P. myriotylum, P. ultimum*) on soybean and so forth.

Accordingly, they can be used as fungicides applicable to a plowed field, orchard, tea-garden, mulberry-garden, meadow, lawn and so on.

The α-hydroxyethylphosphinates (I), which may be racemic or optically active, can be produced by various procedures, of which typical examples are as follows:

Procedure (a):

An α-hydroxyethylphosphinic acid of the formula:

$$XCH_2-\underset{\underset{OH}{|}}{CH}-\underset{\underset{H}{|}}{\overset{\overset{O}{\|}}{P}}-OH \qquad (II)$$

wherein X is as defined above is reacted with an alcohol of the formula:

$$ROH \qquad (III)$$

wherein R is as defined above to give the α-hydroxyethylphosphinate (I). The reaction is usually carried out by treating the α-hydroxyethylphosphinic acid (II) with the alcohol (III) in an amount of 1.0 to 10 equivalents with respect to the α-hydroxyethylphosphinic acid (II) in a solvent in the presence or absence of a catalyst at a temperature of the boiling point of the solvent for 1 to 24 hours.

Procedure (b):

An α-hydroxyethylphosphinate of the formula:

$$XCH_2-\underset{\underset{OH}{|}}{CH}-\underset{\underset{H}{|}}{\overset{\overset{O}{\|}}{P}}-OR' \qquad (I')$$

wherein R' is an alkyl group or a cycloalkyl group and X is as defined above is reacted with the alcohol (III) to give the α-hydroxyethylphosphinate (I). The reaction is normally effected by treating the α-hydroxyethylphosphinate (I') with the alcohol (III) in an amount of 1.0 to 10 equivalents with respect to the α-hydroxyethylphosphinate (I') in a solvent in the presence or absence of a catalyst at a temperature of 60° to 150° C. for 1 to 24 hours.

Procedure (c):

The α-hydroxyethylphosphinic acid (II) is reacted with a diazoalkane of the formula:

$$R''-N_2 \qquad (IV)$$

wherein R″ is a methyl group or an ethyl group. The reaction is ordinarily performed by treatment of the α-hydroxyethylphosphinic acid (II) with the diazoalkane (IV) in an amount of 1.0 to 3.0 equivalents with respect to the α-hydroxyethylphosphinic acid (II) in a solvent at a temperature of 0° to 50° C. for 1 to 5 hours.

The produced α-hydroxyethylphosphinates (I) may be subjected to usual work-up or, if necessary, to purification by chromatography, recrystallization or distillation.

In the above procedures, examples of the alcohol (III) are an alkanol (e.g. methanol, ethanol, propanol, isopropanol, butanol, 1-methylpropanol, 2-methylpropanol, pentanol, 1-methylbutanol, 1-ethylpropanol, 3-methylbutanol, 2-methylbutanol, 1,2-dimethylpropanol, hexanol, 1-methylpentanol, heptanol, 1-methylhexanol, 1-ethylpentanol, octanol, 1-methylheptanol, nonanol, decanol, undecanol, dodecanol, tridecanol), a cycloalkanol (e.g. cyclopropanol, 2-methylcyclopropanol, cyclobutanol, 2-methylcyclobutanol, cyclopentanol, 2-methylcyclopentanol, cyclohexanol, 2-methylcyclohexanol, 3-methylcyclohexanol, 4-methylcyclohexanol, 4-ethylcyclohexanol), a haloalkanol (e.g. 2-fluoroethanol, 2-chloroethanol, 2-boromoethanol, 3-chloroethanol), an alkoxyalkanol (e.g. 2-methoxyethanol, 2-ethoxyethanol, 2-isopropoxyethanol, 3-methoxypropanol), an alkoxyalkoxyalkanol (e.g. 2-(2-methoxyethoxy)ethanol, 2-(2-butoxyethoxy)ethanol), an alkylthioalkanol (e.g. 2-methylthioethanol, 2-ethylthioethanol, 2-isopropylthioethanol), an aralkyloxyalkanol (e.g. 2-benzyloxyethanol, 2-(2-phenylethoxy)ethanol, 2-(4-chlorobenzyloxy)ethanol, 2-(1-naphthylmethoxy)ethanol), a cycloalkylalkanol (e.g. cyclohexylmethanol, 2-cyclohexylethanol), an aralkylthioalkanol (e.g. 2-benzylthioethanol, 2-(4-methylbenzylthio)ethanol), an aryloxyalkanol (e.g. 2-phenoxyethanol, 3-phenoxypropanol, 2-(4-chclophenoxy)ethanol), an arylthioalkanol (e.g. 2-phenylthioethanol, 4-phenylthiobutanol, 2-(1-naphthylthio)ethanol), a halocycloalkanol (e.g. 2-chlorocyclohexanol, 4-bromocyclohexanol), an alkoxycycloalkanol (e.g. 2-methoxycyclohexanol, 4-methoxycyclohexanol), an alkylthiocycloalkanol (e.g. 4-methylthiocyclohexanol, 4-ethylthiocyclohexanol), a cycloalkylcycloalkanol (e.g. 4-cyclohexylcyclohexanol, 2-cyclopentylcyclopentanol), a benzyl alcohol (e.g. benzyl alcohol, 2-fluorobenzyl alcohol, 3-fluorobenzyl alcohol, 4-fluorobenzyl alcohol, 2-chlorobenzyl alcohol, 3-chlorobenzyl alcohol, 4-chlorobenzyl alcohol, 2-bromobenzyl alcohol, 3-bromobenzyl alcohol, 4-bromobenzyl alcohol, 2-iodobenzyl alcohol, 3-iodobenzyl alcohol, 4-iodobenzyl alcohol, 2-methylbenzyl alcohol, 3-methylbenzyl alcohol, 4-methylbenzyl alcohol, 2-ethylbenzyl alcohol, 3-ethylbenzyl alcohol, 4-ethylbenzyl alcohol, 4-isopropylbenzyl alcohol, 4-t-butylbenzyl alcohol, 2methoxybenzyl alcohol, 3-methoxybenzyl alcohol, 4-methoxybenzyl alcohol, 2-ethoxybenzyl alcohol, 3-ethoxybenzyl alcohol, 4-ethoxybenzyl alcohol, 2-propoxybenzyl alcohol, 3-propoxybenzyl alcohol, 4-propoxybenzyl alcohol, 2-isopropoxybenzyl alcohol, 3-isopropoxybenzyl alcohol, 4-isopropoxybenzyl alcohol, 4-butoxybenzyl alcohol, 3-phenoxybenzyl alcohol, 4-phenoxybenzyl alcohol, 4-phenylbenzyl alcohol, 2,4-dichlorobenzyl alcohol, 2,3-dichlorobenzyl alcohol, 2,5-dichlorobenzyl alcohol, 2,6-dichlorobenzyl alcohol, 3,4-dichlorobenzyl alcohol, 3,5-dichlorobenzyl alcohol, 3-trifluoromethylbenzyl alcohol, 2-fluoro-6-chlorobenzyl alcohol, 2,3-dimethoxybenzyl alcohol, 2,4-dimethoxybenzyl alcohol, 2,5-dimethoxybenzyl alcohol, 3,4-dimethoxybenzyl alcohol, 3,5-dimethoxybenzyl alcohol, 2,3,4-trimethoxybenzyl alcohol, 2,4,5-trimethoxybenzyl alcohol, 3,4,5-trimethoxybenzyl alcohol, 2,4,6-trimethoxybenzyl alcohol), a phenethyl alcohol (e.g. 1-phenylethanol, 2-phenylethanol, 1-(4-chlorophenyl)ethanol, 1-(2-fluorophenyl)ethanol, 1-(3-bromophenyl)ethanol, 1-(3,4-dichlorophenyl)ethanol, 1-(4-methylphenyl)ethanol, 1-(4-methoxyphenyl)ethanol, 1-(3-trifluoromethylphenyl)ethanol, 1-(2-chloro-4-bromophenyl)ethanol, 1-(3,4,5-trimethoxyphenyl)ethanol, 2-(4-methylphenyl)ethanol, 2-(4-chlorophenylethanol, 2-(2-methoxyphenyl)ethanol, 2-(4-methoxyphenyl)ethanol, 2-(2,4-dichlorophenyl)ethanol), a phenylpropyl alcohol (e.g. 1-phenylpropanol, 2-phenylpropanol, 3-phenylpropanol), a naphthyl alcohol (e.g. 1-naphthylmethanol, 2-naphthylmethanol, 2-(b 1-naphthylethanol), an anthracenyl alcohol (e.g. 9-antracenyl alcohol), etc. Any of these alcohols can simultaneously play a role of the solvent for the reaction medium.

Preferred examples of the solvent in the procedure (a) or (b) are aromatic hydrocarbons (e.g. benzene, toluene, xylene), halogenated hydrocarbons (e.g. chlorobenzene), aliphatic hydrocarbons (e.g. hexane, heptane, ligroin), etc. Favorable examples of the solvent in the procedure (c) are ethers such as diethyl ether, diisopropyl ether, tetrahydrofuran, dioxane, 1,2-dimethoxyethane, etc. They may be employed alone or in combination.

Examples of the catalyst which may be used in the procedure (a) or (b) are mineral acids (e.g. hydrochloric acid, sulfuric acid).

The starting racemic α-hydroxyethylphosphinic acid (II) can be produced according to the method disclosed in Annales, de Chimie et de Physique., 23, 289–362 (1891). They can be also produced by reacting an acetal of the formula:

$$XCH_2CH(OR')_2 \quad (V)$$

wherein X and R′ are each as defined above with aqueous phosphinic acid in the presence of an acid catalyst (e.g. hydrochloric acid, sulfuric acid), usually at a temperature of 10° to 100° C. for 5 to 24 hours. The amount of the phosphinic acid may be 1.0 to 10 equivalents with respect to the acetal (V).

Some typical examples of the production of the α-hydroxyethylphosphinic acid (II) are shown in the following Reference Examples.

REFERENCE EXAMPLE 1

A solution of chloroacetaldehyde dimethylacetal (124.5 g) and phosphinic acid (50%, 132 g) was heated at 50° to 60° C. for 26 hours in the presence of conc. hydrochloric acid (10 ml). The resultant mixture was concentrated in vacuo to give 140 g (96.7%) of α-hydroxy-β-chloroethylphosphinic acid. $n_D^{22.0}$ 1.4970.

REFERENCE EXAMPLE 2

A solution of bromoacetaldehyde diethylacetal (197 g) and phosphinic acid (50%, 132.0 g) was heated at 60° to 70° C. for 48 hours in the presence of sulfuric acid (0.5 g). The resultant mixture was concentrated in vacuo to give 187.0 g (98.9%) of α-hydroxy-β-bromoethylphosphinic acid. $n_D^{23}$ 1.5105.

The optically active α-hydroxyethylphosphinates (I) can be produced by using an optically active α-hydroxyethylphosphinic acid (II) in the above mentioned procedures.

Practical and presently preferred embodiments for production of the α-hydroxyethylphosphinates (I) are shown in the following Examples.

EXAMPLE 1

A solution of α-hydroxyethylphosphinic acid (2.2 g) and 1-butanol (5.0 g) in benzene (30 ml) was heated for 3 hours with removal of water through a Dean-Stark apparatus. After cooling, the reaction mixture was washed with water, dried over magnesium sulfate and concentrated in vacuo to give 2.71 g (81.6%) of n-butyl α-hydroxyethylphosphinate (Compound No. 5).

EXAMPLE 2

A 10% solution of diazomethane in ether was gradually added to a stirred and ice-cooled solution of α-hydroxyethylphosphinic acid (3.0 g) in tetrahydrofuran (10 ml) until the color of the solution turned to yellow. After 10 minutes, the solvent was evaporated in vacuo. The residue was distilled to give 2.28 g (67.3%) of methyl α-hydroxyethylphosphinate (Compound No. 1).

EXAMPLE 3

A solution of Compound No. 1 (1.03 g) in ethanol (5 g) was heated under reflux for 5 hours. The solvent was evaporated in vacuo, and the residue was distilled to give 430 mg (38.47%) of ethyl α-hydroxyethylphosphinate (Compound No. 2).

EXAMPLE 4

In the same manner as in Example 2 but using (+)-α-hydroxyethylphosphinic acid (400 mg; $[\alpha]_D = +15.2°$ (H$_2$O)), there was prepared 188 mg of methyl (+)-α-hydroxyethylphosphinate ($[\alpha]_D = +6.7°$ (CHCl$_3$)).

EXAMPLE 5

In the same manner as in Example 2 but using (−)-α-hydroxyethylphosphinic acid (340 mg; $[\alpha]_D = -15.5°$ (H$_2$O)), there was prepared 184 mg of methyl (−)-α-hydroxyethylphosphinate ($[\alpha]_D = -7.1°$ (CHCl$_3$)).

EXAMPLE 6

A solution of α-hydroxyethylphosphinic acid (5.5 g) and benzyl alcohol (2.26 g) in benzene (50 ml) was heated for 8 hours with removal of water through a Dean-Stark apparatus. After cooling, the reaction mixture was washed with water, dried over magnesium sulfate and concentrated in vacuo to give 3.65 g (91.2%) of benzyl α-hydroxyethylphosphinate (Compound No. 36).

EXAMPLE 7

A solution of α-hydroxyethylphosphinic acid (5.5 g) and 4-chloro-α-phenethyl alcohol (1.56 g) in benzene (50 ml) was heated for 10 hours with removal of water through a Dean-Stark apparatus. The same work-up as in Example 6 gave 2.38 g (95.7%) of 4-chloro-α'-phenethyl α-hydroxyethylphosphinate (Compound No. 68).

EXAMPLE 8

A solution of α-hydroxy-β-chloroethylphosphinic acid (2.9 g) and 1-butanol (10.0 g) in benzene (30 ml) was heated for 3 hours with removal of water through a Dean-Stark apparatus. The same work-up as in Example 6 gave 2.60 g (64.8%) of n-butyl α-hydroxy-β-chloroethylphosphinate (Compound No. 82).

EXAMPLE 9

A solution of α-hydroxy-β-bromoethylphosphinic acid (1.9 g) in tetrahydrofuran (10.0 g) was treated with diaxomethane in ether until the color of the solution turned to yellow. The same work-up as in Example 2 gave 1.70 g (83.7%) of methyl α-hydroxy-β-bromoethylphosphinate (Compound No. 88).

Some examples of the α-hydroxyethylphosphinates (I) produced as above are shown in Table 1.

TABLE 1

| Compound No. | X | R | Physical constant |
|---|---|---|---|
| 1 | H | CH$_3$ | $n_D^{24}$ 1.4563 (98–100° C./0.15 mmHg) |
| 2 | H | C$_2$H$_5$ | $n_D^{20}$ 1.4552 (93–96° C./0.06 mmHg) |
| 3 | H | n-C$_3$H$_7$ | $n_D^{20.0}$ 1.4535 |
| 4 | H | i-C$_3$H$_7$ | $n_D^{25}$ 1.4502 |
| 5 | H | n-C$_4$H$_9$ | $n_D^{22}$ 1.4485 |
| 6 | H | i-C$_4$H$_9$ | $n_D^{19}$ 1.4462 |
| 7 | H | n-C$_5$H$_{11}$ | $n_D^{20}$ 1.4505 |
| 8 | H | i-C$_5$H$_{11}$ | $n_D^{21}$ 1.4505 |
| 9 | H | n-C$_6$H$_{13}$ | $n_D^{20}$ 1.4515 |
| 10 | H | n-C$_7$H$_{15}$ | $n_D^{20.0}$ 1.4503 |
| 11 | H | n-C$_8$H$_{17}$ | $n_D^{20.0}$ 1.4572 |
| 12 | H | n-C$_{10}$H$_{21}$ | $n_D^{19.0}$ 1.4561 |
| 13 | H | FCH$_2$CH$_2$ | $n_D^{25.0}$ 1.4528 |
| 14 | H | ClCH$_2$CH$_2$ | $n_D^{18.0}$ 1.4743 |
| 15 | H | ClCH$_2$CH$_2$CH$_2$ | $n_D^{21.0}$ 1.4650 |
| 16 | H |  | $n_D^{20}$ 1.4730 |
| 17 | H |  | $n_D^{20.0}$ 1.4752 |
| 18 | H | CH$_3$OCH$_2$CH$_2$ | $n_D^{20.0}$ 1.4428 |
| 19 | H | C$_2$H$_5$OCH$_2$CH$_2$ | $n_D^{20.0}$ 1.4435 |
| 20 | H | i-C$_3$H$_7$OCH$_2$CH$_2$ | $n_D^{18.0}$ 1.4480 |
| 21 | H | CH$_3$SCH$_2$CH$_2$ | $n_D^{20.0}$ 1.4980 |
| 22 | H | C$_2$H$_5$SCH$_2$CH$_2$ | $n_D^{20.0}$ 1.4885 |
| 23 | H |  | $n_D^{20.0}$ 1.5665 |
| 24 | H |  | $n_D^{20.0}$ 1.5188 |
| 25 | H |  | $n_D^{20.0}$ 1.5260 |
| 26 | H |  | $n_D^{20.0}$ 1.5630 |
| 27 | H |  | $n_D^{20.0}$ 1.4460 |
| 28 | H |  | $n_D^{20.0}$ 1.4722 |
| 29 | H |  | $n_D^{20}$ 1.4690 |
| 30 | H | sec-C$_4$H$_9$ | $n_D^{20}$ 1.4460 |

TABLE 1-continued

| Compound No. | X | R | Physical constant |
|---|---|---|---|
| 31 | H | 2-Cl-cyclohexyl | $n_D^{21}$ 1.5633 |
| 32 | H | 4-CH₃S-cyclohexyl | $n_D^{20}$ 1.5565 |
| 33 | H | 2-OCH₃-cyclohexyl | $n_D^{20}$ 1.5230 |
| 34 | H | cyclohexyl-cyclohexyl | $n_D^{20}$ 1.5650 |
| 35 | H | CH₃OCH₂CH₂OCH₂CH₂ | $n_D^{20}$ 1.4900 |
| 36 | H | C₆H₅—CH₂ | $n_D^{20.0}$ 1.5325 |
| 37 | H | 2-F-C₆H₄—CH₂ | $n_D^{20.0}$ 1.5112 |
| 38 | H | 3-F-C₆H₄—CH₂ | $n_D^{19.5}$ 1.5085 |
| 39 | H | 4-F-C₆H₄—CH₂ | $n_D^{20.0}$ 1.5100 |
| 40 | H | 2-Cl-C₆H₄—CH₂ | $n_D^{20.0}$ 1.5490 |
| 41 | H | 3-Cl-C₆H₄—CH₂ | $n_D^{19.5}$ 1.5500 |
| 42 | H | 4-Cl-C₆H₄—CH₂ | $n_D^{21.0}$ 1.5453 |
| 43 | H | 2-Br-C₆H₄—CH₂ | $n_D^{20.0}$ 1.5638 |
| 44 | H | 3-Br-C₆H₄—CH₂ | $n_D^{19.5}$ 1.5651 |
| 45 | H | 4-Br-C₆H₄—CH₂ | M.P. 58–61° C. |
| 46 | H | 3-I-C₆H₄—CH₂ | $n_D^{20.0}$ 1.5720 |
| 47 | H | 2-CH₃-C₆H₄—CH₂ | $n_D^{20.0}$ 1.5261 |
| 48 | H | 3-CH₃-C₆H₄—CH₂ | $n_D^{20.0}$ 1.5290 |
| 49 | H | 4-CH₃-C₆H₄—CH₂ | $n_D^{19.5}$ 1.5286 |
| 50 | H | 4-C₂H₅-C₆H₄—CH₂ | $n_D^{20.5}$ 1.5310 |
| 51 | H | 4-i-C₃H₇-C₆H₄—CH₂ | $n_D^{19.5}$ 1.5102 |
| 52 | H | 4-t-C₄H₉-C₆H₄—CH₂ | $n_D^{20.0}$ 1.5150 |
| 53 | H | 2-OCH₃-C₆H₄—CH₂ | $n_D^{19.5}$ 1.5320 |
| 54 | H | 3-CH₃O-C₆H₄—CH₂ | $n_D^{19.5}$ 1.5335 |
| 55 | H | 4-CH₃O-C₆H₄—CH₂ | $n_D^{20.5}$ 1.5390 |
| 56 | H | 4-n-C₃H₇O-C₆H₄—CH₂ | $n_D^{20.0}$ 1.5432 |
| 57 | H | 4-n-C₄H₉O-C₆H₄—CH₂ | $n_D^{20.5}$ 1.5436 |
| 58 | H | 4-C₂H₅O-C₆H₄—CH₂ | $n_D^{20.0}$ 1.5420 |
| 59 | H | 3-C₆H₅O-C₆H₄—CH₂ | $n_D^{20.0}$ 1.5488 |
| 60 | H | 4-C₆H₅-C₆H₄—CH₂ | Waxy material |
| 61 | H | 2,4-Cl₂-C₆H₃—CH₂ | $n_D^{19.0}$ 1.5632 |
| 62 | H | 3,5-Cl₂-C₆H₃—CH₂ | $n_D^{20.0}$ 1.5537 |
| 63 | H | 3,5-(CH₃)₂-C₆H₃—CH₂ | $n_D^{19.5}$ 1.5258 |

TABLE 1-continued

| Compound No. | X | R | Physical constant |
|---|---|---|---|
| 64 | H | 2,4-dimethoxybenzyl (CH₃O, OCH₃ on benzyl-CH₂) | $n_D^{20.0}$ 1.5236 |
| 65 | H | 3,4,5-trimethoxybenzyl (CH₃O, CH₃O, CH₃O on benzyl-CH₂) | $n_D^{20.0}$ 1.5350 |
| 66 | H | α-methylbenzyl (phenyl-CH(CH₃)) | $n_D^{20.0}$ 1.5256 |
| 67 | H | α-ethylbenzyl (phenyl-CH(C₂H₅)) | $n_D^{19.5}$ 1.5225 |
| 68 | H | 1-(4-chlorophenyl)ethyl (Cl-C₆H₄-CH(CH₃)) | $n_D^{20.0}$ 1.5460 |
| 69 | H | phenyl-CH₂CH₂ | $n_D^{17.0}$ 1.5278 |
| 70 | H | phenyl-CH(CH₃)-CH₂ | $n_D^{19.5}$ 1.5210 |
| 71 | H | 4-Cl-C₆H₄-CH₂CH₂ | $n_D^{20.0}$ 1.5390 |
| 72 | H | 2-OCH₃-C₆H₄-CH₂CH₂ | $n_D^{20.0}$ 1.5286 |
| 73 | H | 4-CH₃O-C₆H₄-CH₂CH₂ | $n_D^{21.0}$ 1.5248 |
| 74 | H | 4-CH₃-C₆H₄-CH₂CH₂ | $n_D^{19.0}$ 1.5185 |
| 75 | H | phenyl-CH₂CH₂CH₂ | $n_D^{19.5}$ 1.5220 |
| 76 | H | 1-naphthylmethyl | $n_D^{20.0}$ 1.5705 |
| 77 | H | 2-naphthyl-CH₂CH₂ | $n_D^{20.0}$ 1.5653 |
| 78 | H | 9-anthrylmethyl | $n_D^{20.0}$ 1.5750 |
| 79 | Cl | CH₃ | $n_D^{25}$ 1.4562 |
| 80 | Cl | C₂H₅ | $n_D^{25}$ 1.4555 |
| 81 | Cl | n-C₃H₇ | $n_D^{25}$ 1.4530 |
| 82 | Cl | n-C₄H₉ | $n_D^{23}$ 1.4560 |
| 83 | Cl | i-C₄H₉ | $n_D^{27}$ 1.4458 |
| 84 | Cl | sec-C₄H₉ | $n_D^{27}$ 1.4482 |
| 85 | Cl | n-C₅H₁₁ | $n_D^{27}$ 1.4465 |
| 86 | Cl | i-C₅H₁₁ | $n_D^{27}$ 1.4430 |
| 87 | Cl | n-C₆H₁₃ | $n_D^{27}$ 1.4425 |
| 88 | Br | CH₃ | $n_D^{25}$ 1.5050 |
| 89 | Br | C₂H₅ | $n_D^{25}$ 1.5005 |
| 90 | Br | n-C₃H₇ | $n_D^{25.0}$ 1.4905 |
| 91 | Br | i-C₃H₇ | $n_D^{25.0}$ 1.4865 |
| 92 | Br | n-C₄H₉ | $n_D^{25}$ 1.4935 |
| 93 | Br | i-C₄H₉ | $n_D^{25.0}$ 1.4890 |
| 94 | Br | sec-C₄H₉ | $n_D^{25}$ 1.4860 |
| 95 | Br | n-C₅H₁₁ | $n_D^{25}$ 1.4749 |
| 96 | Cl | cyclohexyl | $n_D^{25}$ 1.4912 |
| 97 | Br | cyclopentyl | $n_D^{25}$ 1.4960 |
| 98 | Cl | ClCH₂CH₂ | $n_D^{25}$ 1.5095 |
| 99 | Br | ClCH₂CH₂ | $n_D^{25}$ 1.5100 |
| 100 | Cl | FCH₂CH₂ | $n_D^{25}$ 1.5001 |
| 101 | Cl | CH₃OCH₂CH₂ | $n_D^{25}$ 1.4950 |
| 102 | Cl | C₂H₅OCH₂CH₂ | $n_D^{25}$ 1.4865 |
| 103 | Br | CH₃OCH₂CH₂ | $n_D^{25}$ 1.5115 |
| 104 | Br | i-C₃H₇OCH₂CH₂ | $n_D^{25}$ 1.5105 |
| 105 | Br | i-C₅H₁₁ | $n_D^{25}$ 1.4723 |

In actual application as fungicides, the α-hydroxyethylphosphinates (I) may be used alone without incorporation of other ingredients. For easier application, however, they are normally employed in admixture with solid or liquid carriers or diluents. The fungicidal compositions can be formulated into any of the ordinarily adopted forms such as, for example, dusts, granules, wettable powders, emulsifiable concentrates, fine particles, aqueous solutions, oil sprays, aerosols and tablets. Such compositions generally contain 0.1 to 99.9% by weight, preferably 2.0 to 80.0% by weight, of the active ingredient.

As the solid carriers or diluents usable for formulation of the fungicidal composition, there may be exemplified plant carriers (e.g. wheat flour, tobacco powder, soybean powder, walnut-shell powder, wooden powder, saw dust, wheat bran, bark dust, cellulose powder, extract residue), fibrous products (e.g. paper, cardboard, rag), crushed synthetic resins, clays (e.g. kaolin, bentonite, terra alba), talcs, other inorganic minerals (e.g. pyrophyllite, celicite, pumice, sulfur powder, diatomaceous earth, white carbon, activated carbon), chemical fertilizers (e.g. ammonium sulfate, ammonium phosphate, ammonium nitrate, urea, ammonium chloride), etc. As the liquid carriers or diluents, there may be employed water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. methylformamide, dimethylacetamide), halogenated hydrocarbons (e.g. dichloroethane, trichloroethylene, carbon tetrachloride), etc.

In addition to the solid or liquid carriers or diluents as exemplified above, there may be used surfactants when desired. Examples of the surfactants are polyoxyethylene phenylphenol polymer, polyoxyethylene aklylaryl ether, sodium laurylsulfate, calcium alkylbenzenesulfonate, alkylsulfates, alkylsulfonates, alkylarylsulfonates, polyethyleneglycol ethers, polyvalent alcohol esters, etc. There may be also used adhesive agents, dispersing agents, stabilizers, etc. Specific examples thereof include casein, gelatin, starch, carboxymethyl cellulose, gum arabic, alginate, calcium ligninsulfonate, bentonite, molasses, polyvinyl alcohol, palm oil, agar, acid isopropyl phosphate, tricresyl phosphate, tall oil, epoxylated oil, surfactants, aliphatic acids and their esters, etc.

Moreover, the fungicidal composition may comprise other fungicides, insecticides, nematocides, acaricides, insect repellents, plant growth regulators, herbicides, fertilizers, soil improvers, etc.

Some typical examples of the fungicidal composition of this invention are shown below. In those examples, part(s) and % are by weight unless otherwise indicated.

EXAMPLE A

Compound No. 37 (2 parts), clay (88parts) and talc (10 parts) were thoroughly pulverized and mixed together to obtain a dust containing 2% of the active ingredient.

EXAMPLE B

Compound No. 6 (30 parts), diatomaceous earth (45 parts), white carbon (20 parts), a wetting agent (sodium laurylsulfate) (3 parts) and a dispersing agent (calcium ligninsulfonate) (2 parts) were thoroughly pulverized and mixed together to obtain a wettable powder containing 30% of the active ingredient.

EXAMPLE C

Compound No. 45 (50 parts), diatomaceous earth (45 parts), a wetting agent (calcium alkylbenzenesulfonate) (2.5 parts) and a dispersing agent (calcium ligninsulfonate) (2.5 parts) were thoroughly pulverized and mixed together to obtain a wettable powder containing 50% of the active ingredient.

EXAMPLE D

Compound No. 18 (20 parts), xylene (60 parts) and an emulsified (polyoxyethylene phenylphenol polymer type) (20 parts) were mixed together to obtain an emulsifiable concentrate containing 20% of the active ingredient.

EXAMPLE E

Compound No. 1 (50 parts), water (45 parts) and a wetting agent (polyoxyethylene alkylaryl ether type) (5 parts) were mixed together to obtain an aqeous solution containing 50% of the active ingredient.

A suitable amount of the fungicidal composition of the invention to be applied is generally from 10 to 1000 grams in terms of the active ingredient per 10 are. In case of the composition form such as a wettable powder, emulsifiable concentrate or aqueous solution, it is normally diluted with water and then applied. The concentration of the active ingredient upon application is preferably within the range of 0.1 to 1% by weight. In case of the composition form such as dust or granules, it is ordinarily applied as such. Since, however, the amount and concentration largely depend upon the composition forms, application times, application methods, application sites, diseases and crops, they may be increased or decreased appropriately.

The following examples show some typical test results supporting the excellent fungicidal activity of the α-hydroxyethylphosphinates (I). In these examples, the compound numbers correspond to those in Table 1. The compounds used for comparison are as follows:

| Compound No. | Structure | Remarks |
|---|---|---|
| A | Tetrachloroisophthalonitrile (Cl₄-benzene with two CN groups) | Commercially available fungicide "chlorothalonil" |
| B | $[CH_3CH_2O-P(=O)(H)-O^-]_3 Al^{3+}$ | Commercially available fungicide "alliete" |
| C | $(CH_2-NH-CS-S^-)_2 Zn^{2+}$ | Commercially available fungicide "zineb" |
| D | $(CH_2-NH-CS-S^-)_2 Mn^{2+}$ | Commercially available fungicide "maneb" |

EXAMPLE I

Seeds of cucumber (species: "sagamihanjiro") were sowed in soil filled in plastic pots and cultivated in a greenhouse for 14 days to obtain seedlings of cucumber having cotyledons. An aqueous dilution of the test compound in the form of an emulsifiable concentrate or wettable powder was applied onto the seedlings of foliar treatment. Then, the seedlings were grown in the greenhouse for 5 days. A spore suspension of Pseudoperonospora cubensis was sprayed onto the seedlings, which were placed at 20° C. under a humid condition for 3 days and then grown at 20° C. under the irradiation with a fluorescent lamp for 3 days. The state of infection of the test plants was observed, and the preventive value was calculated according to the following equation:

| Infection index | State of infection |
|---|---|
| 0 | No infectious spot on leaf |
| 0.5 | Infectious spots of less than 5% of the area of leaf |
| 1 | Infectious spots of less than 20% of the area of leaf |
| 2 | Infectious spots of less than 50% of the area of leaf |
| 4 | Infectious spots of not less than 50% of the area of leaf |

$$\text{Degree of infection (\%)} = \frac{\Sigma\{(\text{Infection index}) \times (\text{number of leaves})\}}{(\text{Total number of leaves}) \times 4} \times 100$$

$$\text{Preventive value (\%)} = 100 - \frac{(\text{Degree of infection in medicated plot})}{(\text{Degree of infection in non-medicated plot})} \times 100$$

The results are shown in Table 2.

TABLE 2

| Compound No. | Concentration of active ingredient (ppm) | Preventive value (%) |
|---|---|---|
| 1 | 200 | 100 |
| 2 | 200 | 100 |

TABLE 2-continued

| Compound No. | Concentration of active ingredient (ppm) | Preventive value (%) |
| --- | --- | --- |
| 3 | 200 | 100 |
| 4 | 200 | 100 |
| 5 | 200 | 100 |
| 6 | 200 | 100 |
| 7 | 200 | 100 |
| 8 | 200 | 100 |
| 9 | 200 | 95 |
| 10 | 200 | 90 |
| 11 | 200 | 75 |
| 12 | 200 | 100 |
| 13 | 200 | 100 |
| 14 | 200 | 100 |
| 15 | 200 | 100 |
| 16 | 200 | 100 |
| 17 | 200 | 100 |
| 18 | 200 | 100 |
| 19 | 200 | 100 |
| 20 | 200 | 100 |
| 21 | 200 | 100 |
| 22 | 200 | 100 |
| 23 | 200 | 100 |
| 24 | 200 | 100 |
| 25 | 200 | 100 |
| 26 | 200 | 100 |
| 27 | 200 | 100 |
| 28 | 200 | 100 |
| 29 | 200 | 100 |
| 30 | 200 | 100 |
| 36 | 200 | 100 |
| 37 | 200 | 100 |
| 40 | 200 | 100 |
| 47 | 200 | 100 |
| 48 | 200 | 100 |
| 50 | 200 | 100 |
| 53 | 200 | 100 |
| 55 | 200 | 100 |
| 58 | 200 | 95 |
| 64 | 200 | 90 |
| 66 | 200 | 100 |
| 69 | 200 | 100 |
| 74 | 200 | 100 |
| 75 | 200 | 100 |
| 76 | 200 | 85 |
| 80 | 200 | 100 |
| 82 | 200 | 95 |
| 84 | 200 | 100 |
| 88 | 200 | 100 |
| 89 | 200 | 100 |
| 91 | 200 | 100 |
| 94 | 200 | 93 |
| 97 | 200 | 91 |
| 100 | 200 | 100 |
| 105 | 200 | 100 |
| B | 200 | 44 |

EXAMPLE II

Seeds of cucumber (species: "*sagamihanjiro*") were sowed in soil filled in plastic pots and cultivated in a greenhouse for 14 days to obtain seedlings of cucumber having cotyledons. The seedlings were treated by soil-drench with an aqueous dilution of the test compound in the form of an emulsifiable concentrate or wettable powder. After 4 days, a spore suspension of *Pseudoperonospora cubensis* was sprayed onto the seedlings, which were placed at 20° C. under a humid condition for 3 days and then grown at 20° C. under irradiation with a fluorescent lamp for 4 days. The state of infection of the plants was observed, and the preventive value was calculated as in Example I. p The results are shown in Table 3.

TABLE 3

| Compound No. | Amount of active ingredient (g/are) | Preventive value (%) |
| --- | --- | --- |
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 10 | 100 | 100 |
| 13 | 100 | 100 |
| 14 | 100 | 100 |
| 16 | 100 | 100 |
| 18 | 100 | 100 |
| 19 | 100 | 100 |
| 21 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66 | 100 | 100 |
| 67 | 100 | 100 |
| 68 | 100 | 100 |
| 69 | 100 | 100 |
| 70 | 100 | 100 |
| 71 | 100 | 100 |
| 72 | 100 | 100 |
| 73 | 100 | 100 |
| 74 | 100 | 100 |
| 75 | 100 | 100 |
| 76 | 100 | 100 |
| 77 | 100 | 100 |
| 78 | 100 | 100 |
| 79 | 100 | 100 |
| 80 | 100 | 100 |
| 81 | 100 | 100 |
| 82 | 100 | 100 |
| 83 | 100 | 100 |
| 84 | 100 | 100 |
| 85 | 100 | 100 |
| 86 | 100 | 100 |
| 87 | 100 | 100 |
| 88 | 100 | 100 |
| 89 | 100 | 100 |
| 90 | 100 | 100 |
| 91 | 100 | 100 |
| 92 | 100 | 100 |
| 93 | 100 | 100 |
| 94 | 100 | 100 |
| 95 | 100 | 100 |
| 96 | 100 | 100 |
| 97 | 100 | 100 |
| 98 | 100 | 100 |
| 99 | 100 | 100 |
| 100 | 100 | 100 |
| 101 | 100 | 100 |

TABLE 3-continued

| Compound No. | Amount of active ingredient (g/are) | Preventive value (%) |
|---|---|---|
| 102 | 100 | 100 |
| 103 | 100 | 100 |
| 104 | 100 | 100 |
| 105 | 100 | 100 |
| A | 100 | 0 |
| B | 100 | 25 |

EXAMPLE III

Seeds of grape (species: "*delaware*") were sowed in soil filled in plastic pots and cultivated in a greenhouse for 1 month to obtain seedlings of grape at the 2 to 3-leaved stage. A spore suspension of *Plasmopara viticola* was sprayed onto the seedlings, which were placed at 23° C. under a humid condition for 2 days. Then, an aqueous dilution of the test compound in the form of an emulsifiable concentrate or wettable powder was applied onto the seedlings by foliar treatment. Thereafter, the seedlings were grown at 23° C. under irradiation with a fluorescent lamp for 14 days. The state of infection of the plants was observed, and the preventive value was calculated as in Example I.

The results are shown in Table 4.

TABLE 4

| Compound No. | Concentration of active ingredient (ppm) | Preventive value (%) |
|---|---|---|
| 1 | 500 | 100 |
| 2 | 500 | 100 |
| 3 | 500 | 100 |
| 4 | 500 | 100 |
| 13 | 500 | 100 |
| 14 | 500 | 100 |
| 16 | 500 | 100 |
| 18 | 500 | 100 |
| 36 | 500 | 100 |
| 37 | 500 | 100 |
| 39 | 500 | 100 |
| 40 | 500 | 100 |
| 43 | 500 | 100 |
| 47 | 500 | 100 |
| 50 | 500 | 100 |
| 53 | 500 | 100 |
| 54 | 500 | 100 |
| 61 | 500 | 100 |
| 66 | 500 | 100 |
| 68 | 500 | 100 |
| 74 | 500 | 100 |
| 76 | 500 | 100 |
| 79 | 500 | 100 |
| 80 | 500 | 100 |
| 88 | 500 | 100 |
| 89 | 500 | 100 |
| 91 | 500 | 100 |
| 96 | 500 | 100 |
| 100 | 500 | 100 |

TABLE 4-continued

| Compound No. | Concentration of active ingredient (ppm) | Preventive value (%) |
|---|---|---|
| B | 500 | 69 |
| C | 1000 | 0 |

EXAMPLE IV

Seeds of potato (species: "*danshaku*") were sowed in soil filled in plastic pots and cultivated in a greenhouse for 2 months to obtain seedlings of potato. A spore suspension of *Phytophthora infestans* was sprayed onto the seedlings, which were placed at 20° C. under a humid condition for 20 hours. Then, an aqueous dilution of the test compound in the form of an emulsifiable concentrate or wettable powder was applied onto the seedlings by foliar treatment. Thereafter, the seedlings were grown at 20° C. under a humid condition for 6 days. The state of infection of the plants was observed, and the preventive value was calculated as in Example I.

The results are shown in Table 5.

TABLE 5

| Compound No. | Concentration of active ingredient (ppm) | Preventive value (%) |
|---|---|---|
| 1 | 500 | 95 |
| 2 | 500 | 90 |
| 3 | 500 | 90 |
| 5 | 500 | 93 |
| 8 | 500 | 91 |
| 13 | 500 | 95 |
| 14 | 500 | 97 |
| 16 | 500 | 92 |
| 18 | 500 | 95 |
| 21 | 500 | 90 |
| 36 | 500 | 90 |
| 38 | 500 | 95 |
| 42 | 500 | 85 |
| 43 | 500 | 91 |
| 54 | 500 | 93 |
| 66 | 500 | 87 |
| 71 | 500 | 90 |
| 74 | 500 | 91 |
| 80 | 500 | 87 |
| 88 | 500 | 83 |
| 89 | 500 | 90 |
| 95 | 500 | 93 |
| 99 | 500 | 95 |
| D | 1000 | 0 |

What is claimed is:

1. A compound of the formula:

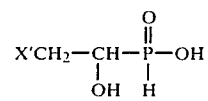

wherein X′ is a chlorine atom or a bromine atom.

* * * * *